United States Patent
Oettel et al.

(12)

(10) Patent No.: US 6,670,350 B1
(45) Date of Patent: Dec. 30, 2003

(54) METHOD OF ADMINISTERING DIENOGEST IN HIGH DOSAGES TO REDUCE THE BODY OF THE BREAST AND PHARMACEUTICAL COMPOSITION FOR SAME

(75) Inventors: Michael Oettel, Jena (DE); Claudia Moore, Drackendorf (DE); Adolf Eduard Schindler, Essen (DE); Bernd Christensen, Essen (DE)

(73) Assignee: JenaPharm GmbH & Co. KG, Jena (DE)

( * ) Notice: Subject to any disclaimer, the term of this patent is extended or adjusted under 35 U.S.C. 154(b) by 0 days.

(21) Appl. No.: 09/913,554

(22) PCT Filed: Feb. 8, 2000

(86) PCT No.: PCT/EP00/00982

§ 371 (c)(1),
(2), (4) Date: Jan. 14, 2002

(87) PCT Pub. No.: WO00/48604

PCT Pub. Date: Aug. 24, 2000

(30) Foreign Application Priority Data

Feb. 18, 1999 (DE) .......................... 199 08 762

(51) Int. Cl.$^7$ ............................... A61K 31/56
(52) U.S. Cl. .................. 514/178; 514/177; 514/179
(58) Field of Search ................ 514/177, 178, 514/179

(56) References Cited

U.S. PATENT DOCUMENTS 5,652,231 A * 7/1997 Shibutani et al. .......... 514/179

FOREIGN PATENT DOCUMENTS

DE 32 38 984 A 5/1983
GB 2109231 A * 6/1983 ............ A61K/9/06

OTHER PUBLICATIONS

Greenblatt et al. CAPLUS Abstract, "A new progestogen: the 18–homolog of norethisterone," Clin. Pharmacol. Therap. (1966), 7 (4), 490–500, AN 1966:449444, 1966.*

Oettel, M., et al: A 19–Norrprogestin Without 17Alpha–Ethinyl . . . , Drugs Today/Medicamentois De Actualidad, Es, J.R. Prous SS, A., International Publishers, BD. 31, NR. 7, Oct. 1, 1995, Seite 528, 529.

Pasqualini Jr et al: :Progestins: Present and Future J Steroid Biochem Molec Biol, BD. 59, NR. 5/6 1996, Seiten 357–363.

Foster RH and Wilde MI: "Dienogest", Drugs, BD. 56, Nov., 1998, Seiten 825–833.

* cited by examiner

*Primary Examiner*—Shengjun Wang
(74) *Attorney, Agent, or Firm*—Michael J. Striker

(57) ABSTRACT

A method of administering dienogest to a women in high dosages for reducing the body of the breast is described. The dosage should be at least ten times the effective dosage for inhibiting ovulation in the women. A pharmaceutical composition for use in the method is also described. Furthermore, retrogression of mastopathic changes in the body of the breast can be brought about. Dienogest is also outstandingly suitable for the prophylaxis of mastopathies. In high dosages, dienogest prevents the formation of mastopathic changes in the body of the breast.

4 Claims, No Drawings

METHOD OF ADMINISTERING DIENOGEST IN HIGH DOSAGES TO REDUCE THE BODY OF THE BREAST AND PHARMACEUTICAL COMPOSITION FOR SAME

This application is a 371 of PCT/EP00/00982, filed Feb. 8, 2000, which claim the foreign priority of Germany application 19908762.8, filed Feb. 18, 1999.

The present invention relates to the use of dienogest in high dosages for the reduction of the body of the breast.

BACKGROUND OF THE INVENTION

Enlargements of the body of the breast occur very frequently in sexually mature women, especially in those aged between 35 and 50 years. Depending on the form of the mastopathy, whether it be a simple, slightly proliferating or an atypically proliferating mastopathy, such changes are also associated with an increased risk of breast cancer. Aside from this increased risk of cancer, other symptoms also occur, such knotty hardenings, pain and secretions. The premenstrual intensification of these symptoms is characteristic here.

Treatment of the mastopathies generally is not required, since the breast as such is healthy, although considerably enlarged at times.

In the state of the art, hormone treatments are described, for which various gestagens are used alone or in combination with estrogens for the prophylaxis or treatment of breast cancer in women.

In the DE 40 19 670 A1, a pharmaceutical preparation for the treatment of menopause is described. This is a mixture of estrogen and gestagen, with the progesterone derivative, chlormadinone acetate, as gestagen content.

The DE 197 05 229 A1 discloses an agent for hormonal contraception with three hormone components, which are also suitable for the treatment and/or prophylaxis of tumors of the mammary grand. The agent comprises a first hormone component, which comprises at least one synthetic estrogen, a second hormone component, which comprises at least one biogenic estrogen and a third hormone component, which comprises at least a gestagen for the continuous and combined administration.

WO 9010462 describes a combination therapy for the treatment of diseases, sensitive to treatment with estrogen. In the case of breast cancer or endometrial cancer, treatment with an anti-estrogen and at least one further component from the group comprising androgens, progestins, inhibitors of the formation of sex hormones, inhibitors of prolactin secretion, inhibitors of growth hormone secretion and inhibitors of ACTH secretion, are described.

In the EP 0 654 267 A1, the use of dienogest as a carcinostatic agent for hormone therapy is described. The treatment or prophylaxis of uterine or cervical cancer and/or of breast cancer is described here.

SUMMARY OF THE INVENTION

The known hormonal therapies for the treatment of breast cancers have a series of disadvantages. For example, it is not possible to reduce the healthy bodies of the breast or to carry out a prophylaxis of mastopathies. It is an object of the present invention therefore, to make a new hormone therapy available, which overcomes these disadvantages.

Pursuant to the invention, this objective is accomplished by the use of dienogest in large dosage for reducing the body of the breast.

The objective furthermore is accomplished by the use of dienogest in high dosages for the preparation of pharmaceutical compositions for reducing the body of the breast.

Pursuant to the invention, the use of dienogest is preferred, the dosage being at least 10 times the ovulation dose.

Particularly preferred is the use of dienogest in an at least once daily dosage of at least 10 mg of dienogest.

Especially preferred is the use of dienogest for a period of at least three months.

Pursuant to the invention, dienogest furthermore is used with oral, transdermal, vaginal, subcutaneous, intramuscular or intravenous application.

Dienogest (17-hydroxy-3-oxo-19-nor-17α-pregna-4,9-diene-21-nitrile, dienogestril) is a gestagen and a synthetic derivative of hydroxyprogesterone. Dienogest is used in many contraceptives as a gestagen component.

Surprisingly, it was found that an increased dose of dienogest, which is a multiple of that required to inhibit ovulation, is able to reduce the body of the breast. Furthermore, it was found that retrogressions of mastopathic changes of the body of the breast are brought about. Furthermore, it was also found that dienogest is suitable outstandingly also for the prophylaxis of mastopathies. In high dosages, dienogest prevents the formation of mastopathic changes of the body of the breast.

Surprisingly, it was furthermore found that blood fat values are affected advantageously by the administration of high dosages of dienogest. When dienogest is used pursuant to the invention, the HDL cholesterol level is increased. This leads to a positive effect on the cardiovascular system and the risk of coronary diseases is decreased.

Pharmaceutical preparations for the oral, transdermal, vaginal, subcutaneous, intravenous or intramuscular application, which contain, in addition to the usual vehicles and diluents, also dienogest as an active ingredient, are also an object of the present invention.

The pharmaceutical products of the invention are produced by known procedures with the usual solid or liquid vehicles or diluents and the customarily employed pharmaceutical adjuvants, depending on the type of application desired, and in a suitable dosage. The preferred preparations consist of a pharmaceutical form, which is suitable for oral applications. Such pharmaceutical forms are, for example, tablets, film tablets, coated tablets, capsules, pills, powders, solutions or suspensions or sustained release forms.

Of course, parenteral preparations, such as injection solutions, also come into consideration. Furthermore, suppositories, especially vaginal suppositories, are named as examples of preparations.

Appropriate tablets can be obtained, for example, by mixing the active ingredients with known adjuvants, for example, with inert diluents such as dextrose, sugar, sorbitol, mannitol, polyvinylpyrrolidone, disintegrants such as corn starch or alginic acid, binders such as starch or gelatin, lubricants such as magnesium stearate or talcum and/or means for achieving a sustained release effect, such as carboxypolymethylene, carboxymethylcellulose, cellulose acetate phthalate or polyvinyl acetate. The tablets may also consist of several layers.

Correspondingly, coated tablets can be produced by coating cores, which are produced similarly to the tablets, with materials used conventionally in coatings, such as polyvinylpyrrolidone or shellac, gum arabic, talcum, titanium dioxide or sugar. The coating may also consist of several layers, for which the adjuvants, mentioned above for tablets, can be used.

Solutions or suspensions with the inventive active ingredient may, additionally, contain taste-improving agents such as saccharin, cyclamate or sugar, as well as fragrances, such as vanillin or orange extract. In addition, they may contain suspending agents, such as sodium carboxymethylcellulose or preservatives such as p-hydroxybenzoate. Capsules, which contain active ingredients, may be prepared, for example, by mixing the active ingredient with an inert vehicle such as lactose or sorbitol and encapsulating the mixture in gelatin capsules.

Transdermal forms of application may consist, for example, of plasters containing active ingredients. Such systems are known.

Suitable suppositories, especially for vaginal application, can be prepared, for example, by mixing vehicles intended for this purpose, such as natural fats or polyethylene glycol or their derivatives.

EXAMPLE

In a clinical study, the reduction of the body of the breast was detected sonographically in 21 patients ranging in age from 18 to 52 years.

In each case, 10 mg of dienogest were administered orally as a tablet over a period of 24 weeks at intervals of 12 hours. The daily dose therefore amounted to 20 mg of dienogest. The breast was examined sonographically before the treatment as well as after 12 and 24 weeks of continuous therapy.

In all women, the body of the breast decreased significantly on the average. Symptoms of mastopathic changes, such as duct ectasia, had receded completely.

What is claimed is:

1. A method of reducing the body of a breast of a women not suffer from breast cancer, said method comprising the step of administering to a women in need of such treatment an amount of dienogest effective for reduction of said body of said breast, wherein said amount of said dienogest effective for said reduction of said body of said breast is at least ten times an effective amount of said dienogest required to inhibit ovulation in said women, and wherein said amount of said dienogest effective for said reduction of said body of said breast is administered daily in a plurality of dosage units over a period of at least three months.

2. The method as defined in claim 1, wherein said administering is performed orally, transdermally, vaginally, subcutaneously, intramuscularly or intravenously.

3. A method of reducing the body of a breast of a women not suffer from breast cancer, said method comprising the step of administering to a women in need of such treatment an amount of dienogest effective for reduction of said body of said breast, wherein said amount of said dienogest effective for said reduction of said body of said breast is at least ten times an effective amount of said dienogest required to inhibit ovulation in said women, and wherein said amount of said dienogest effective for said reduction of said body of said breast is administered daily in a plurality of dosage units over a period of at least three months, wherein each of said dosage units is 10 mg of said dienogest and said dosage units are administered orally twice each day over said period of said at least three months.

4. The method as defined in claim 1, wherein said administering is performed orally.

* * * * *